(12) United States Patent
Ihara et al.

(10) Patent No.: US 7,815,932 B2
(45) Date of Patent: Oct. 19, 2010

(54) PATCH CONTAINING FENTANYL FOR MUCOUS MEMBRANE OF ORAL CAVITY

(75) Inventors: Katsumi Ihara, Sanuki (JP); Mitsuhiro Nagata, Takamatsu (JP); Sayoko Inazuki, Naruto (JP)

(73) Assignee: Teikoku Seiyaku Co., Ltd., Kagawa-Ken (JP)

( * ) Notice: Subject to any disclaimer, the term of this patent is extended or adjusted under 35 U.S.C. 154(b) by 769 days.

(21) Appl. No.: 10/524,024

(22) PCT Filed: Jun. 1, 2004

(86) PCT No.: PCT/JP2004/007894

§ 371 (c)(1),
(2), (4) Date: Feb. 9, 2005

(87) PCT Pub. No.: WO2004/110445

PCT Pub. Date: Dec. 23, 2004

(65) Prior Publication Data

US 2005/0232982 A1    Oct. 20, 2005

(30) Foreign Application Priority Data

Jun. 10, 2003    (JP) .............................. 2003-164943

(51) Int. Cl.
 *A61F 13/02* (2006.01)
 *A61F 13/00* (2006.01)
 *A61F 15/00* (2006.01)

(52) U.S. Cl. ...................... 424/448; 424/443; 424/449; 602/41; 602/42; 602/43; 602/46; 602/48; 602/49; 602/52; 602/54; 602/57

(58) Field of Classification Search ................. 424/448, 424/449; 514/317; 602/41–43, 46, 48–49, 602/52, 54, 57
See application file for complete search history.

(56) References Cited

U.S. PATENT DOCUMENTS

| 4,588,580 A | 5/1986 | Gale et al. |
| 4,671,953 A | 6/1987 | Stanley et al. |

(Continued)

FOREIGN PATENT DOCUMENTS

EP    0 873 750    10/1998

(Continued)

OTHER PUBLICATIONS

Abstract of JP 2000-44476 published Feb. 15, 2000.

(Continued)

*Primary Examiner*—Humera N Sheikh
(74) *Attorney, Agent, or Firm*—Wenderoth, Lind & Ponack, L.L.P.

(57) ABSTRACT

To provide a patch containing fentanyl for mucous membrane of the oral cavity (oral transmucosal fentanyl), which rapidly increases the serum concentration of the drug, is easy in handling and is superior in safety. The patch can be prepared by laminating on one side of a drug layer which contains fentanyl or its salt as an active ingredient, methyl vinyl ether-maleic anhydride copolymer as an adhesive, and at least one substance selected from the group consisting of hydroxypropylcellulose, hydroxypropylmethylcellulose and hydroxyethylcellulose as a thickener, a support layer hardly soluble or insoluble in water, and a backing in this order.

8 Claims, 5 Drawing Sheets

U.S. PATENT DOCUMENTS

| | | | |
|---|---|---|---|
| 4,772,470 A * | 9/1988 | Inoue et al. | 424/435 |
| 4,826,686 A * | 5/1989 | Brantl et al. | 424/448 |
| 4,880,416 A | 11/1989 | Horiuchi et al. | |
| 5,113,860 A * | 5/1992 | McQuinn | 600/345 |
| 5,298,017 A * | 3/1994 | Theeuwes et al. | 604/20 |
| 5,672,356 A | 9/1997 | Rault et al. | |
| 5,820,877 A * | 10/1998 | Yamaguchi et al. | 424/449 |
| 6,139,866 A | 10/2000 | Chono et al. | |
| 6,242,004 B1 | 6/2001 | Rault | |
| 2003/0017133 A1 | 1/2003 | Abu-Izza et al. | |
| 2004/0086551 A1* | 5/2004 | Miller et al. | 424/449 |
| 2004/0180080 A1 | 9/2004 | Furusawa et al. | |

FOREIGN PATENT DOCUMENTS

| | | | |
|---|---|---|---|
| EP | 1293199 A1 * | 3/2003 | |
| JP | 61-37725 | 2/1986 | |
| JP | 62-112557 | 5/1987 | |
| JP | 64-071812 | 3/1989 | |
| JP | 10-045570 | 2/1998 | |
| JP | 2002-275066 | 9/2002 | |
| WO | 00/16751 | 3/2000 | |
| WO | 01/87276 A1 * | 11/2001 | |
| WO | WO 01/87276 A1 * | 11/2001 | |

OTHER PUBLICATIONS

Dictionary of Pharmaceutical Additives by Japan Pharmaceutical Additive Counsel, 1994, pp. 234-235.

Supplementary European Search Report issued May 7, 2010 in European Patent Application No. 04 73 5659 corresponding to present US application.

* cited by examiner

PATCH CONTAINING FENTANYL FOR MUCOUS MEMBRANE OF ORAL CAVITY

TECHNICAL FIELD

The present invention relates to a patch containing fentanyl for mucous membrane of the oral cavity (oral transmucosal fentanyl), which is superior in handling on application (pasting), rapidly increases the serum concentration of the drug, is a little in transfer of the drug to a gastrointestinal tract, is easily tore off when it becomes unnecessary, and is superior in safety.

Namely, the present invention relates to the patch containing fentanyl for mucous membrane of the oral cavity, which can be prepared by laminating a drug-layer which contains fentanyl or its salt as an active ingredient and shows adhesivity due to being dissolved in or swelled with water, a support layer hardly soluble or insoluble in water, and a backing in their order.

BACKGROUND ART

Fentanyl or its citrate is a synthetic narcotic analgesic whose analgesic activity is about 100 times higher than that of morphine in the animal test.

Nowadays, the transdermally absorbable and sustained release preparation containing fentanyl for the therapy of cancer pain is commercialized and it retains almost the effective serum concentration for 24 to 72 hours after administration (see Japanese Patent Publication A 61-37725). However, in regard to said transdermally absorbable and sustained release preparation, as the absorption of the drug is mild after administration of it, and the effective serum concentration can not be obtained until 12 to 24 hours after initial administration, it is impossible to expect the quick analgesic effect. Furthermore, even after said transdermally absorbable and sustained release preparation is tore off from the skin, fentanyl remains in the corneum. Therefore, its absorption into body continues, the drug is hardly removed from the body, and the half-life of the serum concentration is long, 17 hours. As such, said transdermally absorbable and sustained release preparation is not suitable for the therapy for acute ache such as pang (breakthrough pain) which occurs while the preparation is continuously applied. Against such pang which occurs while said preparation being continuously applied, the immediately active morphine preparations (injections, oral preparations, suppositories) are additionally administered as a rescue-preparation (a preparation for emergently additional administration) in Japan.

In regard to a transdermally absorbable preparation containing fentanyl, other various preparations are proposed (see Japanese Patent Publication A 2000-44476, and Japanese Patent Publication A 10-45570).

On the other hand, the fentanyl preparation for mucous membrane of the oral cavity which is possible to quickly circulate through the whole body and is noninvasively administered (Trade name: Actiq) is sold in USA (see U.S. Pat. No. 4,671,953). This preparation is a candy-type preparation with a stick (lollipop). When pang occurs, the preparation is put between cheek and submaxillary gingivae and is sucked in a period of 15 minutes to absorb fentanyl citrate from mucous membrane of the oral cavity. The amount of the systemic transfer by absorption of the drug from mucous membrane of the oral cavity is about one fourth. The rest of it is swallowed with saliva and is gradually absorbed from a gastrointestinal tract. In regard to said preparation, the tip of the preparation with a stick must be put between cheek and submaxillary gingivae for 15 minutes to give much uncomfortable feeling in a mouth. However, when it is chewed, the swallowed amount becomes much and the amount absorbed from mucosal membrane of the oral cavity becomes less. When pang disappears, the drug becomes unnecessary and the administration of the drug is stopped. Even if the preparation is taken off from the oral cavity in such a case, the drug which was already transferred into a gastrointestinal tract continues to be absorbed thereafter. Therefore, it is difficult to control the serum concentration of the drug.

In addition, patches containing fentanyl for mucous membrane of the oral cavity are described in Japanese Patent Publication A 2002-275066, etc., but they are not yet put in practice.

DISCLOSURE OF INVENTION

The object of the present invention is to provide a patch containing fentanyl for mucous membrane of the oral cavity, which does not need any complex procedures when the patch is applied, gives a little uncomfortable feeling in the oral cavity, can quickly increases the serum concentration as the drug is absorbed almost at the applied region, makes transfer of the drug into a gastrointestinal tract less by preventing the drug release into other part of the oral cavity except the applied region, is easily tore off when it becomes unnecessary, can easily control the serum concentration of the drug, is usable as a rescue preparation for pang during the therapy for cancer pain and is highly safe.

The present invention relates to a patch containing fentanyl for mucous membrane of the oral cavity, which can be prepared by laminating on one side of a drug layer which contains fentanyl or its salt as an active ingredient, methyl vinyl ether-maleic anhydride copolymer as an adhesive, and at least one substance selected from the group consisting of hydroxypropyl cellulose, hydroxypropyl methylcellulose and hydroxyethyl cellulose as a thickener, a support layer hardly soluble or insoluble in water, and a backing in their order.

The present inventors have been extensively studied in order to solve the above problems and as a result have found that a drug layer which contains fentanyl or its salt as an active ingredient, methyl vinyl ether-maleic anhydride copolymer as an adhesive, and at least one substance selected from the group consisting of hydroxypropyl cellulose, hydroxypropyl methylcellulose and hydroxyethyl cellulose as a thickener shows sufficient adhesivity to mucous membrane of the oral cavity due to the presence of water and easily releases the drug from the applied surface and quickly increases the serum concentration. Furthermore, by laminating a support layer which is insoluble or hardly soluble in water on the opposite side of the adhesive surface of the drug layer, the drug is hardly swallowed with saliva due to protecting to release the drug into the other region in the oral cavity except the applied region, and furthermore, by equipping a backing thereto and making the patch thick in some extend, regardless of smallness of the size, handling of the patch becomes easy, such as picking up, applying or tearing off, and that the patch containing fentanyl for mucous membrane of the oral cavity which is easily controllable the serum concentration is obtained. Thus the present invention has been completed.

EXPLANATION OF SIGNS

1: Drug layer
2: Support layer
3: Backing
4: Liner

BEST MODE FOR CARRYING OUT THE INVENTION

The mode for carrying out the present invention is explained in detail.

The ingredients which are used and if necessary, other ingredients are contained in the preparation of the present invention are explained in detail.

Fentanyl or its salt (the drug) which is contained in the drug layer of the preparation of the present invention is a free-base or an organic or inorganic salt thereof, such as fentanyl citrate, etc. Their combination can be also used, but fentanyl citrate is especially preferably used.

The amount of the drug is 0.01~40 w/w % per total amount of the drug layer, preferably 2~35 w/w %, and more preferably 5~30 w/w %. When the amount is less than 0.01 w/w %, it is impossible to expect sufficient efficacy of the drug. When the amount is beyond 40 w/w %, and other ingredients consisting of the drug layer, the drug and the solvent are mixed, the insoluble materials remain and therefore, it is impossible to prepare the preparation.

The amount of methyl vinyl ether-maleic anhydride copolymer used as an adhesive in the drug layer of the preparation of the present invention is 5~90 w/w % per total weight of the drug layer, preferably 10~70 w/w %, and more preferably 15~60 w/w %.

When the amount is less than 5 w/w %, the adhesivity decreases and it is difficult that the preparation maintains to stick to mucous membrane of the oral cavity, and when the amount is beyond 90 w/w %, the preparation becomes fragile and becomes difficult to keep the shape. Therefore, such amounts are not preferable.

The thickener used in the drug layer of the preparation of the present invention includes a cellulose derivative selected from the group consisting of hydroxypropyl cellulose, hydroxypropyl methylcellulose and hydroxyethyl cellulose, or a combination thereof. Hydroxypropyl cellulose is especially preferably used.

The amount of the thickener is 0.2~80 w/w % per total amount of the drug layer, preferably 1~60 w/w %, and more preferably 2.5~50 w/w %. When the amount is less than 0.2 w/w %, the preparation becomes difficult to keep the shape, and when the amount is beyond 80 w/w %, the preparation becomes difficult to release the drug. Therefore such amounts are not preferable.

A softening agent may be contained in the drug layer of the preparation of the present invention.

The softening agent includes, for example, glycerin, polyethylene glycol (PEG) 200, PEG 300, PEG 400, propylene glycol, etc., or a combination thereof. A combination of glycerin and PEG 400 is especially preferably used and the ratio is preferably 1:1 to 1:5. The amount is 0~50 w/w % per the total amount of the drug layer, preferably 2~40 w/w %, and more preferably 5~30 w/w %. When the amount is beyond 50 w/w %, the drug layer easily collapses and it is difficult that the preparation sufficiently maintains to stick to mucous membrane of the oral cavity. Therefore, such amounts are not preferable.

An absorption promoting agent, such as N-methyl-2-pyrrolidone may be added to the drug layer in order to promote the absorption of the drug from mucous membrane of the oral cavity. The amount is 0~10 w/w % per the total amount of the drug layer, preferably 1~7 w/w %. When the amount is beyond 10 w/w %, there is anxious for irritation to mucous membrane of the oral cavity, the drug layer becomes easily collapsible, and it is difficult that the preparation sufficiently maintains to stick to mucous membrane of the oral cavity. Therefore, such amounts are not preferable.

A sweetening agent may be contained in the drug layer of the preparation of the present invention in order to lessen the bitter taste, such as glycerin, glucose, fructose, maltose, sucrose, D-sorbitol, D-mannitol, xylitol, etc. The amount is 0~30 w/w % per total amount of the drug layer, preferably 2~20 w/w. When the amount is beyond 30 w/w %, the drug layer becomes easily collapsible and it is difficult that the preparation sufficiently maintains to stick to mucous membrane of the oral cavity. Therefore, such amounts are not preferable.

In regard to the preparation of the present invention, the support layer which is insoluble or hardly soluble in water is laminated on the drug layer in order to prevent to release the drug in other part of the oral cavity except the applied region.

As a material which is contained in order to make the support layer the water-insoluble or hardly water-soluble, ethyl cellulose is illustrated. The amount is 40~90 w/w % per total amount of the support layer, preferably 50~75 w/w %. When the amount is less than 40 w/w %, the water-insolubility or hard water-solubility of the support layer greatly decreases, and when the amount is beyond 90 w/w %, it is anxious that the affinity with the drug layer decreases and that the layers are separated. Therefore, such amounts are not preferable.

In order to give the support layer of the present invention the affinity to the drug layer, a thickener can be further added thereto. The thickener includes hydroxypropyl methylcellulose, especially hydroxypropyl methylcellulose 2910, and it can be solely used or in a combination of other hydroxypropyl methylcellulose. The amount is 1~30 w/w % per total amount of the support layer, preferably 5~25 w/w %. When the amount is less than 1 w/w %, it is anxious that the affinity with the drug layer decreases and the layers are separated, and when the amount is beyond 30 w/w %, it becomes difficult to maintain the water-insolubility or water-hardly solubility of the support layer. Therefore, such amounts are not preferable.

To the support layer, a plasticizer may be further added. The plasticizer includes surfactants, such as castor oil, trietyl citrate, polysorbate, etc. The surfactant can be used solely or in a combination of them, and especially castor oil can be preferably used. The amount is 1~50 w/w % per total weight of the drug layer, preferably 2~35 w/w %, and more preferably 5~30 w/w %. When the amount is less than 1 w/w %, the flexibility of the support layer decreases, and when the amount is beyond 50 w/w %, the support layer becomes easily collapsible. Therefore, such amounts are not preferable.

As the backing of the preparation of the present invention, woven or unwoven fabrics, or paper can be used. When woven or unwoven fabrics are used, one or more fabrics selected from biodegradable plastics, polyester, polyethylene and polypropylene represented by aliphatic polyester, such as poly lactic acid, poly glycolic acid, poly lactone, polybutylene succinate, are used, and especially fabrics consisting of poly lactic acid are preferably used.

The drug layer or the support layer of the preparation of the present invention may, if necessary, contain additives, such as a coloring agent like red #102, yellow #4, titanium oxide, etc., a corrective like citric acid, povidone, menthol, etc., an antioxidant like ascorbic acid, disodium edatate, tocopherol acetate, etc., a stabilizer like light silicic acid anhydride, macrogol, etc., a preservative like sodium benzoate, parabens, etc.

The method for preparing the patch containing fentanyl for mucous membrane of the oral cavity of the present invention is not limited, but for example, the following steps are illustrated.

Ingredients contained in the drug layer, when they are liquid, themselves, or when they are solid or very highly viscous, after each of them is dissolved or dispersed in a suitable medium, are mixed under stirring. The mixture is spread on a liner made of polyethylene terephtalate, polypropylene, polyethylene, etc., dried and if necessary, spreading and drying are repeated several times. The procedure is carried so that the thickness of the drug layer after finally drying becomes 20~200 µm.

Next, when ingredients contained in the support layer are liquid, they are mixed under stirring. When the ingredients are solid or highly viscous, they are mixed under stirring, after each of them is dissolved or dispersed in a suitable medium. The mixture is spread on the surface on the opposite side of the liner side of the drug layer. Then thereon is laminated the backing, and if necessary the laminate is stuck under the pressure by a roller, and dried to prepare the preparation so as to have the thicknesses of the support layer and the backing, respectively 1~200 µm and 50~1000 µm. A part or all of ingredients of the support layer can be penetrated into the backing to incorporate with it. If necessary, after the support layer is spread (coated), the drying and spreading may be repeated, but it is preferable to spread on the support layer once.

EXAMPLE

The present invention is explained by illustrating examples, but the present invention is not limited by these examples.

Example 1

According to ingredients of Example 1 shown in Table 1, a drug layer was prepared. Namely, methyl vinyl ether-maleic anhydride copolymer in 80% ethanol, hydroxypropyl cellulose (Viscosity: 150~400 mPa·S) in ethanol, glycerin, N-methyl-2-pyrrolidone and fentanyl citrate were mixed under stirring. The mixture was spread (coated) on a liner made of polyethylene terephtalate and dried to prepare a film having 100 µm in thickness.

According to ingredients of Example 1 shown in Table 2, a support layer was prepared. Namely, ethyl cellulose in ethanol, hydroxypropyl methylcellulose 2910 in 50% ethanol, a dispersion of titanium oxide in ethanol and castor oil were mixed under stirring. The mixture was spread on the surface on the opposite side of the liner side of the drug layer-film. Thereon were laminated unwoven fabrics made of poly lactic acid fiber having 410 µm in thickness as a backing, and the preparation was dried to give an objected patch containing fentanyl for mucous membrane of the oral cavity. The thickness of the support layer was prepared as to be theoretically 25 µm in thickness.

Example 2

Ingredients for a drug layer of Example 2 shown in Table 1, ingredients for a support layer of Example 2 shown in Table 2 and a backing were laminated in the same manner as in Example 1 to prepare an objected patch containing fentanyl for mucous membrane of the oral cavity.

Example 3

Ingredients for a drug layer of Example 3 shown in Table 1, ingredients for a support layer of Example 3 shown in Table 2 and a backing were laminated in the same manner as in Example 1 to prepare an objected patch containing fentanyl for mucous membrane of the oral cavity.

Example 4

Ingredients for a drug layer of Example 4 shown in Table 1, ingredients for a support layer of Example 4 shown in Table 2 and a backing were laminated in the same manner as in Example 1 to prepare an objected patch containing fentanyl for mucous membrane of the oral cavity.

Example 5

Ingredients for a drug layer of Example 5 shown in Table 1, ingredients for a support layer of Example 5 shown in Table 2 and a backing were laminated in the same manner as in Example 1 to prepare an objected patch containing fentanyl for mucous membrane of the oral cavity.

Example 6

Ingredient for a drug layer of Example 6 shown in Table 1, ingredients for a support layer of Example 6 shown in Table 2 and a backing were laminated in the same manner as in Example 1 to prepare an objected patch containing fentanyl for mucous membrane of the oral cavity.

Example 7

Ingredient for a drug layer of Example 7 shown in Table 1, ingredients for a support layer of Example 7 shown in Table 2 and a backing were laminated in the same manner as in Example 1 to prepare an objected patch containing fentanyl for mucous membrane of the oral cavity.

Example 8

Ingredient for a drug layer of Example 8 shown in Table 1, ingredients for a support layer of Example 8 shown in Table 2 and a backing were laminated in the same manner as in Example 1 to prepare an objected patch containing fentanyl for mucous membrane of the oral cavity.

Example 9

Ingredients for a drug layer of Example 9 shown in Table 1, ingredients for a support layer of Example 9 shown in Table 2 and a backing were laminated in the same manner as in Example 1 to prepare an objected patch containing fentanyl for mucous membrane of the oral cavity.

TABLE 1

| Ingredient (weight %) | Example | | | | | | |
|---|---|---|---|---|---|---|---|
| | 1 and 8 | 2 | 3 | 4 | 5 and 9 | 6 | 7 |
| Fentanyl citrate | 19 | 19 | 19 | 19 | 19 | 19 | 19 |
| Methyl vinyl ether-maleic anhydride copolymer | 43 | 43 | 43 | 43 | 43 | 55 | 21 |
| Hydroxypropyl cellulose (Viscosity: 6~10 mPa · S) | — | — | — | — | 21.5 | 15 | — |
| Hydroxypropyl cellulose (Viscosity: 150~400 mPa · S) | 21.5 | 21 | — | 21.5 | — | — | 40 |
| Hydroxypropyl cellulose (Viscosity: 1000~4000 mPa · S) | — | — | 21 | — | — | — | — |
| Glycerin | 2.5 | 3 | 7.5 | 7.5 | 7.5 | 3 | 7.5 |
| Polyethylene glycol 400 | 12.5 | 12 | 7.5 | 7.5 | 7.5 | 6 | 7.5 |
| N-Methyl-2-pyrrolidone | 1.5 | 2 | 2 | 1.5 | 1.5 | 2 | 5 |

TABLE 2

| | Example | | |
|---|---|---|---|
| | 1~7 | 8 | 9 |
| Ingredient (weight %) | | | |
| Ethyl cellulose | 66 | 66 | 70 |
| Hydroxypropyl methylcellulose 2910 | 13.5 | 21 | 7 |
| Castor oil | 17 | 9.5 | 19.5 |
| Titanium oxide | 3.5 | 3.5 | 3.5 |

Test 1

The skin-permeation test in vitro was carried out on the preparation of Example 1 using the transdermally absorbable sustained release preparation as a control.

After removal of hairs of the abdomen of Wistar rats (6~7 weeks, male), the skin was extracted. The body site of the skin was fit as a donor side on a Franz diffusion cell kept at 37° C. The patch containing fentanyl for mucous membrane of the oral cavity of Example 1 was punched in a circle having 25 mm in diameter (containing fentanyl 9 mg). Physiological saline was sprayed on the surface of the drug layer of the circle and the circle was stuck to the skin. The transdermally absorbable sustained release preparation containing 2.5 mg of fentanyl was stuck as a control in the same as the above. Phosphate buffer was filled in the receptor side and the sampling was carried out with variation with time. The amount of fentanyl was measured by HPLC and the permeated amount of fentanyl was calculated. The result was shown in FIG. 2.

Figure 1:
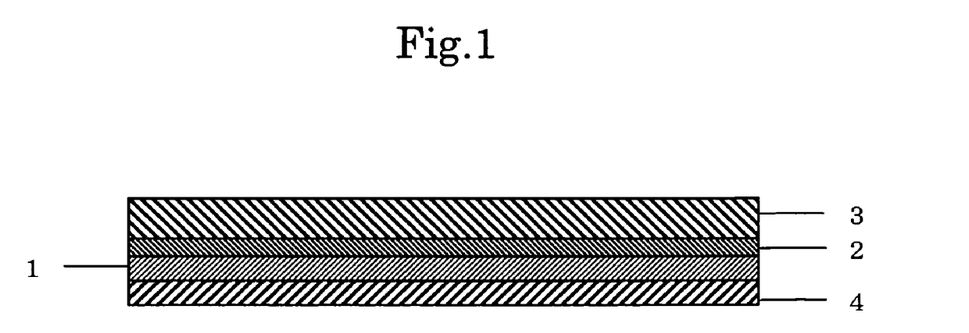
FIG. 1 shows the cross section of a patch containing fentanyl for mucous membrane of the oral cavity of the present invention.
Figure 2:
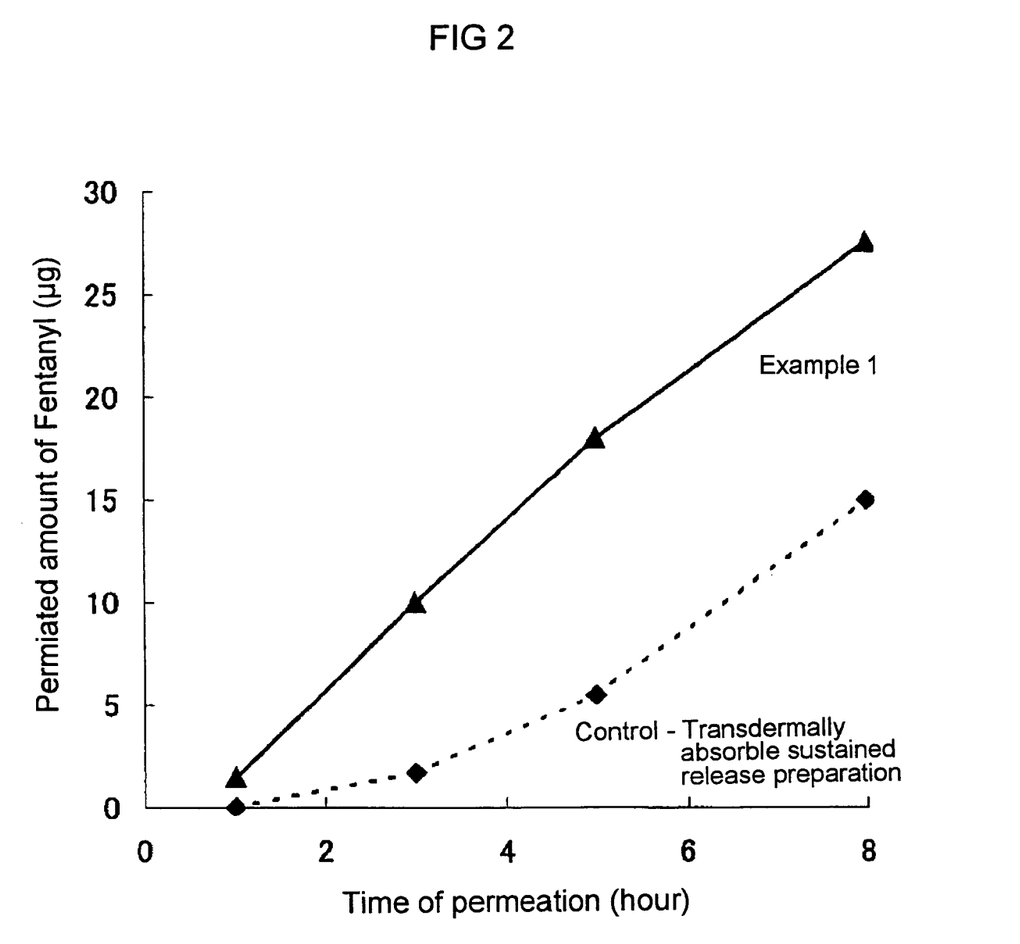
FIG. 2 shows the test result on skin-permeability in vitro by using a preparation of Example 1 of the present invention.

The patch containing fentanyl for mucous membrane of the oral cavity of Example 1 showed quick skin-permeability comparing with the preparation for mucous membrane of the oral cavity as a control.

Test 2

The skin-permeation test in vitro on the preparations of Examples 2 to 5 was carried out on the corneum removed-skin by stripping.

After removing hairs of the abdomen of Wistar rats (6~7 weeks, male), this area was subjected to stripping 5 times by using an adhesive tape and then the skin was extracted. The body site of the skin was fit as a donor side on a Franz diffusion cell kept at 37° C. Each of the patches containing fentanyl for mucous membrane of the oral cavity of Examples 2 to 5 was punched in a circle having 25 mm in diameter (containing fentanyl 9 mg). Physiological saline was sprayed on the surface of the drug layer of the circle and the circle was stuck to the skin. Phosphate buffer was filled in the receptor side and the sampling was carried out with variation with time. The amount of fentanyl was measured by HPLC and the permeated amount of fentanyl was calculated. The result was shown in FIG. 3.

Figure 3:
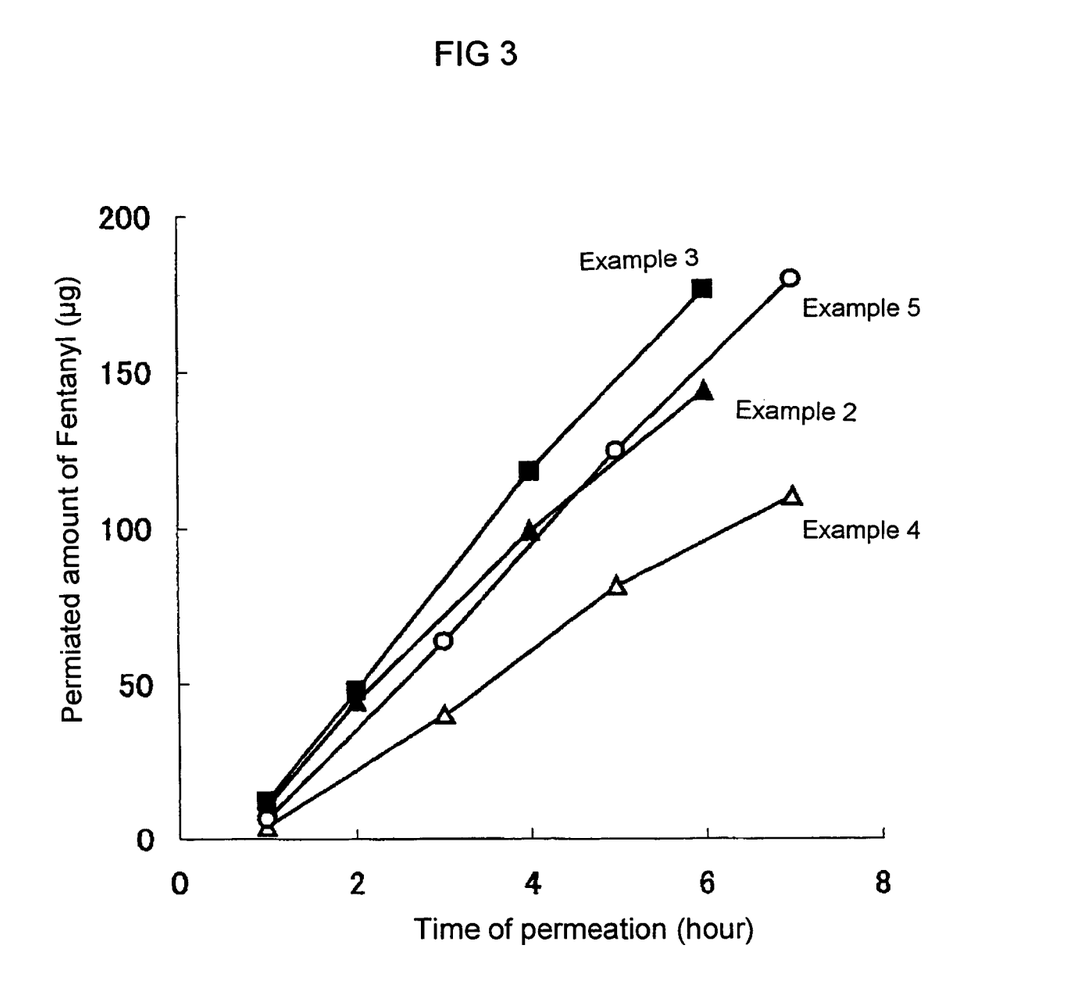
FIG. 3 shows the test result on the permeability in the corneum removed-skin by the stripping method in vitro by using preparations of Examples 2 to 5 of the present invention.

All patches containing fentanyl for mucous membrane of the oral cavity of Examples 2 to 5 showed high skin-permeability on the corneum removed-skin.

Test 3

The serum concentration of fentanyl after applying the preparation of Example 4 to mucous membrane of the oral cavity of a dog was measured.

A patch containing fentanyl for mucous membrane of the oral cavity of Example 4 was punched in an ellipse having 2 $cm^2$ (containing fentanyl 3 mg). Physiological saline was sprayed on the surface of the drug layer of the ellipse and then the ellipse was stuck to an inside of the upper lip of a beagle (weight 15~19 kg, male). The blood was collected from time to time and fentanyl concentration in the serum was measured by HPLC. A patch containing fentanyl for mucous membrane of the oral cavity (containing fentanyl 2.5 mg) was stuck to the skin of the breast of the dog in the same as the above and the variation with time on the serum concentration was compared with the former (see Kyles, et al., American journal of veterinary research Vol. 57, No. 5, page 715~719, 1996).

Figure 4:
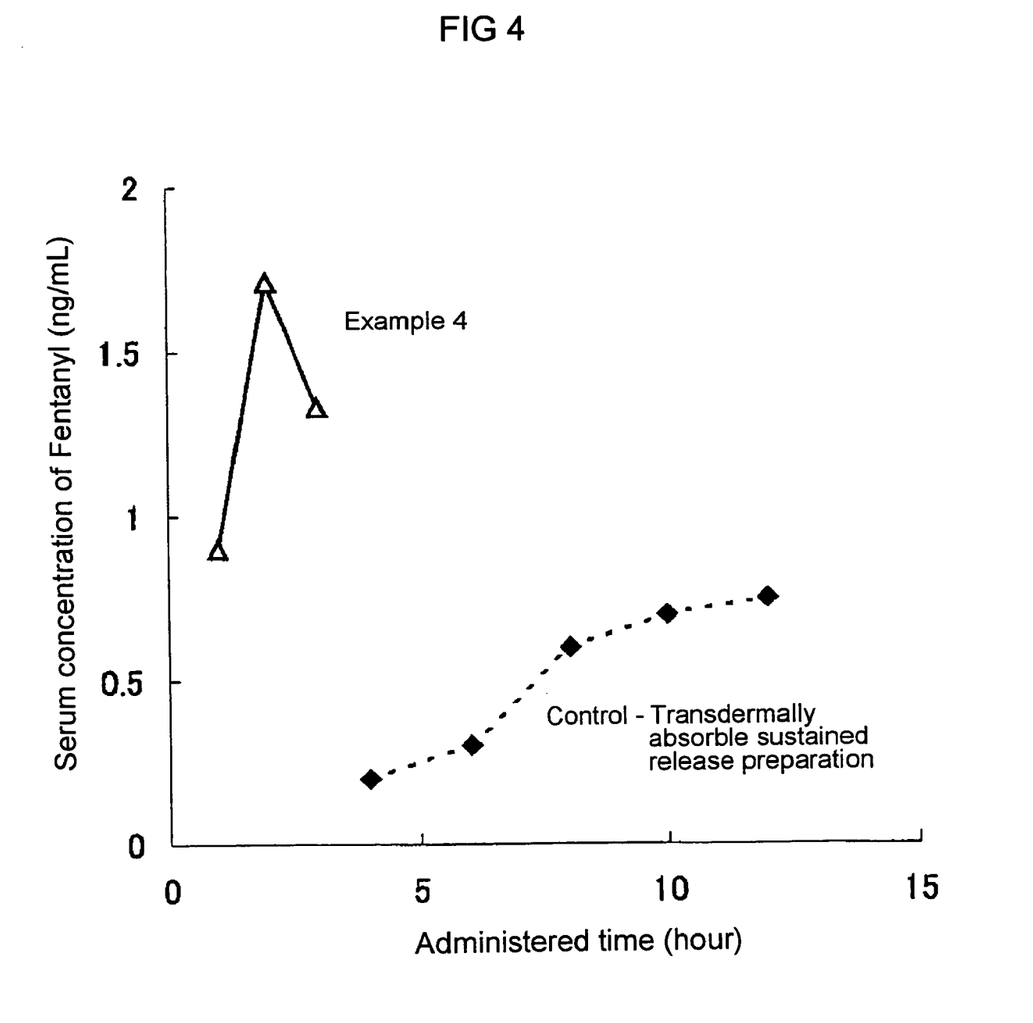
FIG. 4 shows the test result on measurement of the serum concentration of fentanyl after administration of a preparation of Example 4 of the present invention to mucous membrane of the oral cavity of dogs.

The result was shown in FIG. 4. Although the serum concentration mildly rose in regard to the preparation for mucous membrane of the oral cavity as a control, the serum concentration quickly rose and dropped down and the peak concentration was higher in regard to the patch containing fentanyl for mucous membrane of the oral cavity of Example 4.

Test 4

The drug release test was carried out on the preparation of Example 5.

A patch containing fentanyl for mucous membrane of the oral cavity of Example 5 was punched in an ellipse having 2 $cm^2$ (containing fentanyl 3 mg) and the backing-side of the ellipse was stuck on both sides of a paddle for an elution test tool with using a double-sided adhesive tape. Phosphate buffer 500 ml as an elution was put in a vessel and kept at 37° C., and the paddle on which the patch containing fentanyl for mucous membrane of the oral cavity stuck was set at the middle height of the elution and then the paddle was rotated at 50 rpm. At 5, 10, 20, 30 and 60 minutes later after the test began, the elutions were taken, the amounts of fentanyl were measured by HPLC and the ratio of the drug release was calculated. As a control, the drug layer-side of the patch containing fentanyl for mucous membrane of the oral cavity was stuck on the paddle, and the same test as the above was carried out. The result was shown in FIG. 5.

Figure 5:
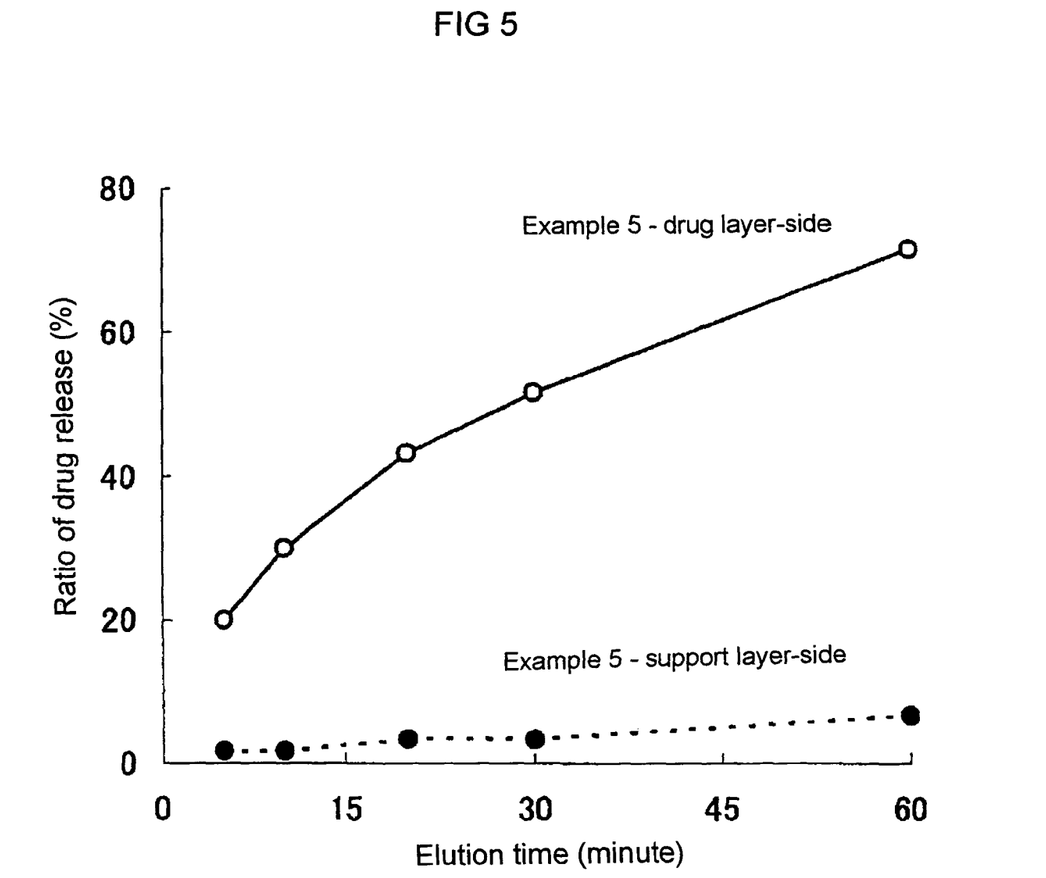
FIG. 5 is the test result of the drug release by using a preparation of Example 5 of the present invention.

The drug release-rate of the patch containing fentanyl for mucous membrane of the oral cavity of Example 5 from the side of the drug layer was about 20% at 5 minutes later after initiation, about 50% at 30 minutes later after initiation, and about 70% at 60 minutes later after initiation, and the quick drug release was observed. As a control, the drug layer-side was stuck on the paddle and the drug release from the backing-side was observed. The slowly rising on the drug release rate was observed, but after 60 minutes, the drug release-rate became low, about one twentieth, and the drug release was considerably refrained due to the support layer which was insoluble or hardly soluble.

INDUSTRIAL APPLICABILITY

According to the present invention, by using the drug layer which contains fentanyl or its salt as an active ingredient, methyl vinyl ether-maleic anhydride copolymer as an adhesive, and at least one substance selected from the group consisting of hydroxypropyl cellulose, hydroxypropyl methylcellulose and hydroxyethyl cellulose as a thickener, can be obtained the preparation which shows sufficient adhesivity to mucous membrane of the oral cavity and can quickly increases the serum concentration due to effectively releasing the drug from the applied surface.

Furthermore, by laminating the support layer which is insoluble or hardly soluble in water on the opposite side of the adhesive surface of the drug layer, the drug release into the other region except the applied region and the drug-transfer into a gastrointestinal tract are lessen and when the patch does not need, a great part of the remained drug can be quickly removed by tearing off the patch.

Furthermore, by equipping the backing thereto and making it sufficiently thick, handling of the preparation becomes easy and its application to and its tearing off from mucous membrane of the oral cavity become easy.

As mentioned above, the patch containing fentanyl for mucous membrane of the oral cavity of the present invention can quickly increase the serum concentration of fentanyl after application to mucous membrane of the oral cavity, and according to the necessity, can be removed and therefore, the serum concentration is easily controlled and the patch is useful for the rescue preparation on pang during the therapy for cancer pain.

The invention claimed is:

1. A patch containing fentanyl for mucous membrane of the oral cavity, which comprises a drug layer, a support layer hardly soluble or insoluble in water comprising ethyl cellulose and hydroxypropyl methylcellulose, on the drug layer, and a backing on the support layer, wherein the drug layer consists essentially of fentanyl or its salt as an active ingredient, methyl vinyl ether-maleic anhydride copolymer as an adhesive agent, and at least one substance selected from the group consisting of hydroxypropyl cellulose, hydroxypropyl methylcellulose and hydroxyethyl cellulose as a thickener.

2. The patch containing fentanyl for mucous membrane of the oral cavity according to claim 1, wherein the fentanyl salt is fentanyl citrate.

3. The patch containing fentanyl for mucous membrane of the oral cavity according to claim 1, wherein the drug release rate from the drug layer is adjusted to become 50% within one hour.

4. The patch containing fentanyl for mucous membrane of the oral cavity according to claim 1, wherein the ratio of the adhesive and the thickener is a range selected from 5:95 to 97:3.

5. The patch containing fentanyl for mucous membrane of the oral cavity according to claim 2, wherein the drug release rate from the drug layer is adjusted to become 50% within one hour.

6. The patch containing fentanyl for mucous membrane of the oral cavity according to claim 1, wherein the drug layer consists of fentanyl or its salt as an active ingredient, methyl vinyl ether-maleic anhydride copolymer as an adhesive agent, at least one substance selected from the group consisting of hydroxypropyl cellulose, hydroxypropyl methylcellulose and hydroxyethyl cellulose as a thickener, and further at least one member selected from the group consisting of a softening agent, an absorption promoting agent and a sweetening agent.

7. A patch containing fentanyl for mucous membrane of the oral cavity, which comprises a drug layer, a support layer hardly soluble or insoluble in water comprising ethyl cellulose and hydroxypropyl methylcellulose, on the drug layer, and a backing on the support layer, wherein the drug layer consists of fentanyl or its salt as an active ingredient, methyl vinyl ether-maleic anhydride copolymer as an adhesive agent, and at least one substance selected from the group consisting of hydroxypropyl cellulose, hydroxypropyl methylcellulose and hydroxyethyl cellulose as a thickener.

8. A patch containing fentanyl for mucous membrane of the oral cavity, which comprises a drug layer, a support layer hardly soluble or insoluble in water comprising ethyl cellulose and hydroxypropyl methylcellulose, on the drug layer, and a backing on the support layer, wherein the drug layer consists essentially of fentanyl or its salt as an active ingredient, methyl vinyl ether-maleic anhydride copolymer as an adhesive agent, and at least one substance selected from the group consisting of hydroxypropyl cellulose, hydroxypropyl methylcellulose and hydroxyethyl cellulose as a thickener and further at least one member selected from the group consisting of a softening agent selected from glycerin and polyethylene glycol, an absorption promoting agent consisting of N-methyl-2-pyrrolidone and a sweetening agent.

* * * * *